United States Patent
Küpper et al.

(10) Patent No.: US 7,351,697 B2
(45) Date of Patent: *Apr. 1, 2008

(54) TUMOR-SPECIFIC VECTOR FOR GENE THERAPY

(76) Inventors: Jan-Heinerr Küpper, Bachstrasse 11, D-72127, Kusterdingen (DE); Ralph Meyer, Rosengarten 7, D-55596, Waldböckelheim (DE); Mirella Meyer-Ficca, Rosengarten 7, D-55596, Waldböckelheim (DE); Reinhard Kandolf, Untere Dornäcker 49, D-72379, Hechingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/186,055

(22) Filed: Jul. 21, 2005

(65) Prior Publication Data

US 2005/0281787 A1 Dec. 22, 2005

Related U.S. Application Data

(60) Division of application No. 10/114,770, filed on Apr. 2, 2002, now Pat. No. 6,936,595, which is a continuation of application No. PCT/EP00/08921, filed on Sep. 13, 2000, now abandoned.

(30) Foreign Application Priority Data

Oct. 4, 1999 (DE) ................ 199 47 668

(51) Int. Cl.
*A61K 48/00* (2006.01)
*C12N 15/86* (2006.01)
*C12N 15/861* (2006.01)
*C12N 15/863* (2006.01)
*C12N 15/867* (2006.01)
*C12N 15/52* (2006.01)
*C12N 15/62* (2006.01)

(52) U.S. Cl. ............... 514/44; 424/93.2; 435/320.1; 435/455; 435/456

(58) Field of Classification Search ............... None
See application file for complete search history.

(56) References Cited

U.S. PATENT DOCUMENTS 5,457,035 A 10/1995 Baum et al.
5,856,153 A 1/1999 Tiraby et al.
6,936,595 B2 * 8/2005 Kupper et al. ............... 514/44

FOREIGN PATENT DOCUMENTS

DE 4444949 11/1996

(Continued)

OTHER PUBLICATIONS

Ali, M., et al. 1994 "The use of DNA viruses as vectors for gene therapy" *Gene Therapy* 1:367-384.

(Continued)

*Primary Examiner*—Scott D. Priebe
(74) *Attorney, Agent, or Firm*—Knobbe, Martens Olson & Bear LLP

(57) ABSTRACT

The invention relates to a vector for the gene therapeutic treatment of tumors, especially in connection with radiotherapy. Said vector is provided with a therapeutic gene in the DNA sequence thereof. The gene is controlled by the promoter for the catalytic subunit of the telomerase or by the promoter for cyclin A.

20 Claims, 2 Drawing Sheets

Adenovirus vector telo prom — Telomerase promoter
T7 prom — T7 promoter
T7 pol — T7 RNA polymerase
gene — Therapeutic gene
pA — Polyadenylation signal
Te — Terminator for T7 RNA polymerase
/∕ — Intermediate sequence
ψ — Packaging signal

FOREIGN PATENT DOCUMENTS

| | | |
|---|---|---|
| DE | 1975984 | 7/1999 |
| DE | 19751587 | 7/1999 |
| WO | WO 96/18737 | 6/1996 |
| WO | WO 98/11207 | 3/1998 |
| WO | WO 98/35028 | 8/1998 |
| WO | WO 99/33998 A2 | 7/1999 |
| WO | WO 99/38992 A1 | 8/1999 |
| WO | WO 99/60142 | 11/1999 |
| WO | WO 00/46355 A2 | 8/2000 |
| WO | WO 00/56909 | 9/2000 |

OTHER PUBLICATIONS

Freytag, et al. 1998 "A novel three-pronged approach to kill cancer cells selectively" Human Gene Ther. 9:1323-1333.

Heise, C., et al. 1997 "ONYX-015, an E1B gene-attenuated adenovirus, causes tumor-specific cytolysis and antitumoral efficacy that can be augmented by standard chemotherapeutic agents" Nature Medicine 3:639-645.

Joki, T. et al. 1995 "Activation of the radiosensitive EGR-1 promoter induces expression of the herpes simplex virus thymidine kinase gene and sensitivity of human glioma cells to ganciclovir." Human Gene Therapy 6:1507-1513.

Koga, S. et al. (2000) " A novel telomerase-specific gene therapy: gene transfer of caspase-8 utilizing the human telomerase catalytic subunit gene promoter" Human Gene Therapy 11:1397-1406.

Majumdar et al. 2000 "HSV TK suicide gene therapy using human telomerase reverse transcriptase (hTERT) promoter" Proc. Amer. Assoc. Cancer Res. Ann. Meeting 41:379, #2406.

Nettelbeck, D.M. et al. 1998 "Cell cycle regulated promoters for the targeting of tumor endothelium" Adv. Exp. Med. Biol. 451:437-440.

Nettelbeck, D.M. et al. 2000 "Gene therapy designer promoters for tumour targeting" Trends in Genetics 16: 174-181.

Pan, C.-X. et al. 1999 "A novel tumor-specific gene therapy for bladder cancer" Medical Hypotheses 53:130-135.

Rothmann, T., et al. 1998 "Replication of ONYX-015, a potential anticancer adenovirus, is independent of p53 status in tumor cells" J. Virol. 72:9470-9478.

Tomanin, R. et al. 1997 "Developement and characterization of a binary gene expression system base on bacteriophage T7 components in adenovirus vectors" Gene 193:129-140.

Uckert, W. et al. 1998 "Double suicide gene (cytosine deaminase and herpes simplex virus thymidine kinase) but not single gene transfer allows reliable elimination of tumor cells in vivo" Human Gene Therapy 9:855-865.

Henglein, B., et al. 1994 "Structure and cell cycle-regulated transcription of the human cyclin A gene." PNAS USA 91:5490-5494.

Horikawa, I., et al. 1999 "Cloning and Characterization of the Promoter Region of Human Telomerase Reverse Trancriptase Gene." Cancer Research 59:826-830.

Takakura, M., et al. 1999 "Cloning of Human Telomerase Catalytic Subunit (hTERT) Gene Promoter and Identification of Proximal Core Promoter Sequences Essential for Transcriptional Activation in Immortalized and Cancer Cells." Cancer Research 59:551-557.

* cited by examiner

TUMOR-SPECIFIC VECTOR FOR GENE THERAPY

RELATED APPLICATIONS

This is a divisional of U.S. patent application Ser. No. 10/114,770, filed Apr. 2, 2002, now U.S. Pat. No 6,936,595, which is a continuation application of International Patent Application PCT/EP00/08921, in which the United States is a designated country, with an international filing date of Sep. 13, 2000, published in German under PCT Article 21(2) and now abandoned, which claims priority to a German Application 19947668.3 filed Oct. 4, 1999, all of which are hereby incorporated by reference.

BACKGROUND OF THE INVENTION

1. Field of the Invention

The present invention relates to a vector for treating tumors by gene therapy, in particular in connection with a radiotherapy, whose DNA sequence has at least one tissue-specific promoter and at least one therapeutic gene whose expression is controlled by the promoter.

2. Related Prior Art

DE 44 44 949 C1 discloses a vector of this type.

For the purposes of the present invention, "tumors" means both malignant and benign tumors.

Malignant neoplastic disorders account for approx. 30% of deaths in the civilized world, and there is at present no safe therapy for any tumor yet, in spite of worldwide efforts over the last decades. Many tumors can be treated only with difficulties, if at all.

Examples of benign tumors include tumors of the vascular wall for which partly the same therapies are used as for the treatment of malignant tumors, i.e. cancer. Such tumors of the vascular wall form as recurring stenoses essentially due to induction of smooth muscle-cell proliferation in the vascular wall caused by "balloon dilatations" (PTCA) for the therapy of local stenoses of the vascular wall which may limit an organ's blood supply. The treatment of such arteriosclerotic disorders includes in addition to balloon dilatation also bypass surgery, stents and other alternative therapeutic methods which, however, likewise have the problem of recurring stenosis, i.e. constriction of the lumen of the treated vessel due to a benign tumor.

Besides surgical removal of both malignant and benign tumors and the treatment thereof with cytostatics, radiotherapy represents from the present point of view one of the most important pillars of tumor therapy. In this connection, the probability of destruction of the tumor depends on the dose administered, with the dose to be administered being limited by the radiosensitivity of normal tissue which inevitably is also irradiated. Therapeutic successes thus depend on the relative radiosensitivity of the tumor cells compared with the cells of the neighboring tissue.

Consequently, an increase in the therapeutic range due to selective radiosensitization of tumor cells would mean a significant step forward in the treatment of tumors and improve the rates of cure. For this reason, pharmacological radiosensitizers which ought to make tumor cells more sensitive to radiation are already in use clinically.

Gene therapy, for the first time, offers the opportunity of achieving significant progress in controlling cancer by making it possible to use therapeutic genes for enhancing radiotherapy or therapy with cytostatics.

In this connection, viral vector systems play a great part in transducing therapeutic genes. Besides retroviral vector systems which, to a certain extent, prefer proliferating cells and very often integrate into the cellular genome, especially adenoviral vector systems which make it possible to attain a high titre of virus particles and which have good transduction efficiency and a very low rate of integration are in discussion; see Ali et al., Gene Ther. (1991), Volume 1, 367-384.

It is crucial for a reliable gene therapy to use the therapeutic gene only in the desired target cells. It would therefore be desirable to use in the gene therapy of tumors a tumor cell-specific promoter which is active in various tumor species and not active in all types of normal tissue. Such a promoter, however, has not yet been found.

In this connection, the initially mentioned DE 44 44 949 C1 describes a vector for the gene therapy of patients who, after surgical removal of a tumor, undergo an aftertreatment using conventional radiation and/or cytostatic methods. The vector contains an expressible DNA insert which is located behind a promoter active in tumor cells and codes for the DNA-binding domain (DBD) of a poly(ADP-ribose) polymerase (PARP). The idea on which that publication is based is to inhibit the activity of the enzyme PARP which is required for repairing damaged DNA by adding DBD molecules so that repair of damaged DNA is prevented.

As example of a tissue-specific promoter the MVM P4 promoter is mentioned. The vector may be a viral vector, and the viruses are replication-incompetent and can be complemented in trans in order to obtain viruses which code for DBD but are unable to propagate in patients.

It has turned out to be a disadvantage of the known vector that the P4 promoter does not yet have the tissue specificity required for a safe gene therapy so that DNA repair is also inhibited in normal tissue, and this is, for reasons that need no further explanation, undesirable.

Most gene therapies therefore include an enhancement of the tumor-specific immune response, i.e. they are a priori systemic, since the local increase in the immune response is not limited to the tumor. At the same time, this is also a desired advantage, because in principle it is also possible to destroy metastases using this therapy.

In order to allow a more or less local gene therapy, the use of retroviruses which transduce genes only into dividing cells has already been discussed. Furthermore, adenovirus mutants were proposed, which ought to replicate only in p53-negative tumor cells; Heise et al., Nat. Med. (1997), Volume 3, 639-645. It is assumed here that all p53-positive cells can prevent proliferation of the adenovirus.

In addition, Joki et al., Hum. Gene Ther. (1995), Volume 6, 1507-1513 have already proposed using radiation-inducible promoters and Nettelbeck et al., Adv. Exp. Med. Biol. (1998), Volume 451, 437-440 proposed using cell cycle-specific promoters.

However, all of these known solutions have specific disadvantages. The concept of immunotherapy has the principal disadvantage that immunosuppressed patients cannot respond to it, the neoplastic disorder itself often additionally adversely affecting the immune system of the said patients. Furthermore, it has turned out that an immunotherapeutic gene or a "suicide gene" which kills the target cell is on its own not sufficient for in vivo administrations; Uckert et al., HUM. GENE THER. (1998), Volume 9, 855-865. The combination of several immunostimulatory genes, where appropriate in connection with suicide genes, has also up to now not led to a breakthrough which would allow a standard application for a given neoplastic disorder.

The abovementioned retroviruses are furthermore not exclusively selective for tumors but infect all dividing cell types, as long as an appropriate receptor is present. Moreover, infection of a healthy cell carries the risk of insertion mutagenesis, since retroviruses integrate into the cellular genome. Replication-competent adenoviruses which have been proposed for a specific tumor therapy are also not specific for tumor cells, as has been proved since then, the effect also being independent of the p53 state; Rothmann et al., J. Virol. (1998), Volume 72, 9470-9478.

The previously described use of suicide genes, too, has disadvantages, since the said suicide genes increase the side effects in healthy proliferating tissues. This problem could be avoided only if the suicide genes were expressed tumor-specifically.

SUMMARY OF THE INVENTION

In view of the above, it is an object of the present invention to provide a vector of the type mentioned at the outset, which acts tumor-specifically and has only slight side effects on normal tissue.

According to the invention, this object is achieved with the vector mentioned at the outset by the promoter being selected from the group comprising the promoter for the catalytic subunit of telomerase and the promoter for cyclin-A.

The object on which the invention is based is completely achieved in this manner.

In fact, the inventors of the present application have recognized that the promoter for the catalytic subunit of telomerase is particularly well suited for a tumor-specific gene therapy. Namely, this promoter which is described, for example, by Horikawa et al., Cancer Res. (1999), Volume 59, 826-830, and Takakura et al., Cancer Res. (1999), Volume 59, 551-557 is very active in tumor cells and more than 90% of all tumors are telomerase-positive. Furthermore, the said promoter is less active in a few proliferative stem cells, for example germ line cells and blood stem cells, and not active at all in the vast majority of proliferative cell types such as, for example, endothelial, fibroblasts, hepatocytes, etc.

In this connection, WO 98/11207 discloses the use of a telomerase promoter in connection with the cell transfection, in order to express products which inhibit cell growth with regard to a cancer treatment. However, the said publication does not mention application of a telomerase promoter in connection with a radiotherapy.

The second promoter used according to the invention is the cyclin-A promoter which is activated in the S phase of the cell cycle, while being repressed in resting cells, i.e. in the G0 and early G1 phases; Henglein et al., PNAS (1994), Volume 91, 5490-5494. Cyclin-A is involved in several regulatory pathways in cell division so that it is exceptionally well suited to expressing therapeutic genes in proliferating cells. Here, the inventors of the present application start from the finding that tumor cells are distinguished in particular by defects in cell cycle regulation and, as a result, enter the S phase in an uncontrolled manner. Choosing the cyclin-A promoter thus would make the therapeutic gene express only in the tumor but not in the surrounding normal tissue, since this tissue in most cases has no or only little proliferative activity.

The cyclin-A promoter in combination with a therapeutic gene is particularly suitable for treating benign tumors, especially in connection with the recurring stenoses mentioned at the beginning, whose therapy is considerably improved by the vector of the invention. Against this background, the present invention also relates to the use of the cyclin-A promoter in connection with a therapy of benign tumors, in particular in connection with recurring stenoses.

Besides the safety provided by the tumor-specific promoters for the catalytic subunit of telomerase and for cyclin-A, a second point of safety results from applying these promoters or the therapeutic genes controlled thereby in connection with a radiotherapy which, according to the current state of the art, can be directed very locally only towards the tumor tissue.

By combining various therapeutic genes which are expressed tissue-specifically and the locally directed radiotherapy, it is possible to provide for the tumor cells to react more sensitively than the neighbouring tissue, albeit perhaps only by a small factor, but as a result the tumor can then be destroyed efficiently.

Besides using the new vector in radiotherapy, it is also an object to use it in connection with chemotherapy, because in this way it is possible to destroy non-localized metastases.

In this connection, preference is given to the therapeutic gene coding for a protein selected from the following group of proteins: cytosine deaminase (CD), herpes simplex-virus thymidine kinase (HSV-TK), DNA-binding domain (DBD) of poly(ADP-ribose) polymerase (PARP), cytotoxic protease 2A and 3C of picomaviruses, preferably of enteroviruses, more preferably of group B Coxsackie viruses (CVB), in particular serotype B3.

Cytosine deaminase converts 5-fluorocytosine to 5-fluorouracil which is incorporated into the DNA of replicating cells and then kills these cells. A systemic 5-fluorocytosine treatment in connection with local radiotherapy leads to a specific increase in the destruction of tumors, since cytosine deaminase is only formed in the tumor cells so that the dreaded side effects such as necroses/fibroses in neighbouring tissue, damage of bone marrow and intestinal mucosa, etc. are avoided.

HSV-TK acts in a similar way; this enzyme activates gancyclovir which likewise incorporates into the DNA of replicating cells and destroys the DNA so that, in connection with local radiotherapy, the same advantages as with CD are attained.

In contrast to CD and HSV-TK, expression of DBD molecules leads to inhibition of the activity of PARP which is required for repairing DNA damage. In this way it is not possible to "repair" again tumor cells "predamaged" in connection with the local radiotherapy, so that they die.

In contrast, the proteases 2A and 3C induce apoptosis in cells and are thus cytotoxic.

The inventors of the present application have now found that by the combination of firstly radiotherapy and secondly of proteins of the above-mentioned type that are tissue-specifically expressed by the two above-mentioned promoters a selective destruction of tumors can be achieved, which is markedly more effective than the individual measures used previously.

In this connection, preference is given to the therapeutic gene being a fusion gene coding for a fusion protein of at least two proteins selected from the abovementioned group of proteins, the therapeutic gene, preferably between the sequence regions for the two proteins, coding for a peptide linker which preferably comprises glycine, in particular 8-10 glycines.

It is advantageous here that a synergistic effect can be achieved if the therapeutic gene contains two suicide genes, with different mechanisms of action of the partners within the fusion proteins in particular producing a synergistic action. The advantage of expressing fusion genes is the possibility of transferring simultaneously two different therapeutic principles and thus producing additive or frequently even synergistic effects in the therapy. In order for the protein domains of the fusion partners to be able to fold optimally for the application, it may be sensible to clone the information for a short peptide linker, preferably 8-10 glycines, between the cDNAs.

Particular preference is given to the following fusion proteins:

CD-linker-HSV-TK, CD-linker-DBD, CD-linker-2A, CD-linker-3C, HSV-TK-linker-DBD, HSV-TK-linker-2A, HSV-TK-linker-3C, DBD-linker-2A and DBD-linker-3C. The order of the fusion partners within a fusion protein may also be reversed.

Overall, preference is given to the vector being based on a virus vector, in particular on an adenovirus vector or an adeno-associated virus vector (AAV).

The invention has as a further object a retrovirus vector coding for the novel vector.

Thus, the novel gene therapy system may be introduced both via conventional viral or non-viral vectors and also via a retrovirus vector into the organism in which it has a substantially more selective effect on the tumor than has previously been possible.

Furthermore, preference is given to providing, between the promoter and the therapeutic gene, a positive-feedback system which is driven by the promoter and controls by itself the expression of the therapeutic gene, the positive-feedback system preferably comprising the T7 promoter and the gene for T7 RNA polymerase, and preference is furthermore given to the promoter controlling the gene for T7 RNA polymerase and the T7 promoter controlling the therapeutic gene, with furthermore a second expression unit being provided, which contains the T7 RNA polymerase under the control of the T7 promoter.

This system of positive feedback causes increased expression of the therapeutic gene in the target cells, with the promoter, i.e. the telomerase or cyclin-A promoter making sure that the positive-feedback system is "triggered" only in the target cells. This positive feedback is based on the finding that the T7 promoter is silent in eukaryotic cells without said T7 RNA polymerase, thus providing a very safe system which multiplies the therapeutic effect without displaying side effects.

In a first expression unit the telomerase promoter, for example, controls T7 RNA-polymerase expression. The second expression unit then contains the T7 promoter which again controls T7 RNA-polymerase expression. In this way, production of T7 RNA polymerase is increased via positive feedback. Since in the third expression unit the therapeutic gene is under the control of the T7 promoter, T7 RNA-polymerase expression by positive feedback also increases expression of the therapeutic gene.

It is understood that the features mentioned above and those still to be illustrated below can be used not only in the combinations indicated in each case but also in other combinations or on their own, without leaving the context of the present invention.

Further features and advantages of the invention arise from the following description of preferred embodiments.

BRIEF DESCRIPTION OF THE DRAWINGS

The examples below are illustrated on the basis of the attached drawing in which.

DESCRIPTION OF PREFERRED EMBODIMENTS

EXAMPLE 1

Figure 1:
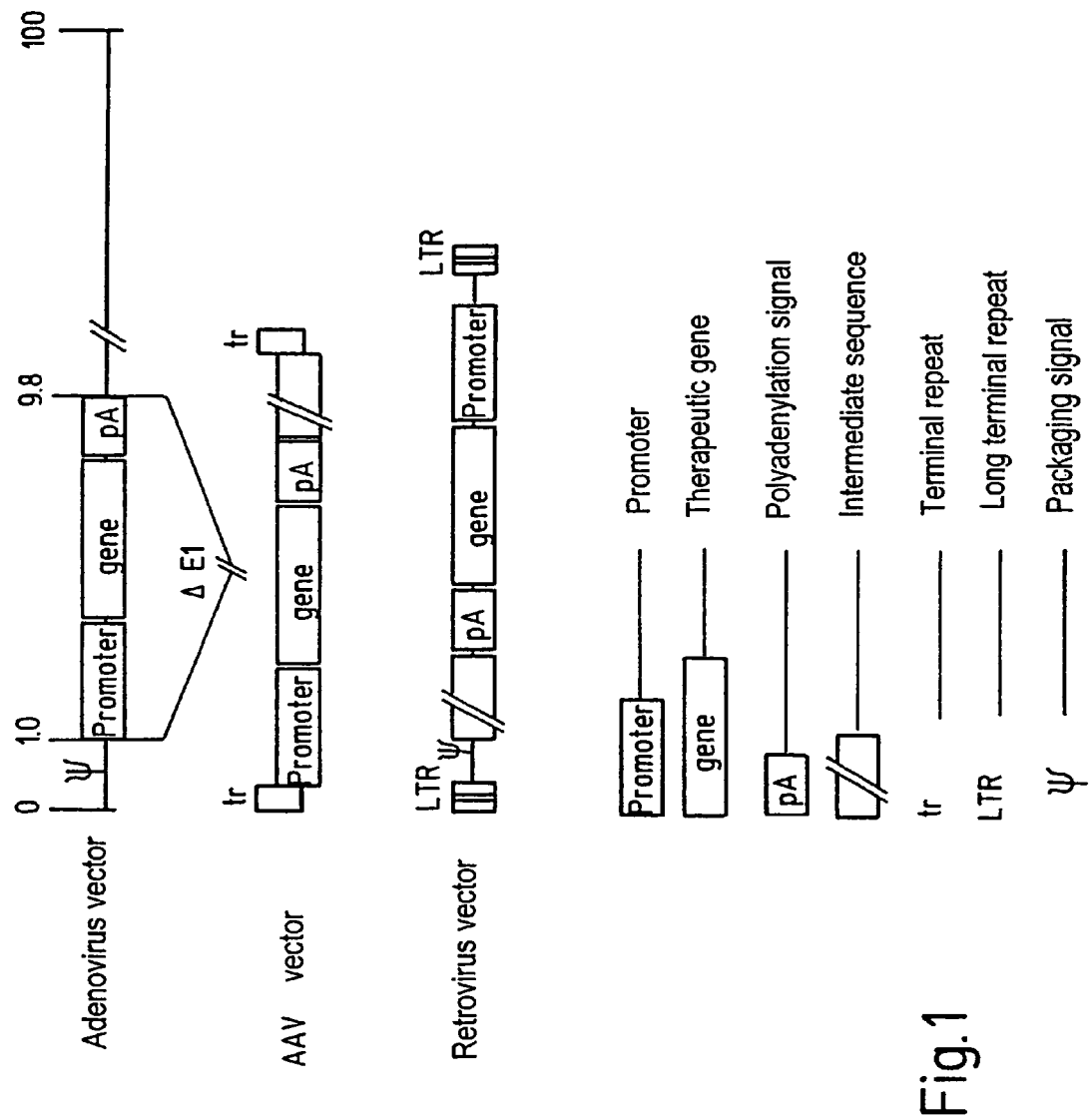
FIG. 1 shows viral vectors for expressing therapeutic genes in tumor cells.

Generation of the Building Blocks for the Viral Vectors 1.1 Telomerase promoter: The telomerase promoter sequence is known; Horikawa et al., loc. cit. and Takakura et al., loc. cit. The promoter may be amplified from cells (e.g. HeLa tumor cells) via PCR using, for example, the following primers:

Forward primer:    ATC AGC TTT TCA AAG ACA CAC

Reverse primer:    CGC GGG GGT GGC CGG GGC GAG 1.2 Cyclin-A promoter: The cyclin-A promoter sequence is like-wise known; Henglein et al., loc. cit. The promoter may be amplified from cells, for example HeLa tumor cells, via PCR using the following primers:

Forward primer:    CGT GTT AAA TAA TTT ATG CAC

Reverse primer:    CAC TGC TCC CGG GAG TGG ACG 1.3 T7 promoter: The T7 RNA-polymerase promoter (approx. 30 bp) may be obtained from plasmid pCR-Script (Stratagene) by BssHI/KpnI digest. The T7-promoter and T7 RNA-polymerase sequences are described, for example, in Dunn and Studier, J. Mol. Biol. (1983), Volume 166, 477-535; GenBank Accession No. V01146, J02518, X00411.

1.4 Cytosine deaminase (CD): The CD gene (1.3 kb) may be obtained from plasmid pcDNA3-CD of the applicant by BamHI/NotI digest. The CD sequence has been described, for example, by Austin and Huber, Mol. Pharmacol. (1993), Volume 43, 380-387; GenBank Accession No. S56903.

1.5 Herpes simplex virus thymidine kinase (HSV-TK): The HSV-TK gene (1.1 kb) can be obtained from plasmid pCDTK of the applicant by BamHI/BglI digest. The HSV-TK sequence is de-scribed by Suzutani et al. in Microbiol. Immunol. (1995), Volume 39, 787-794; GenBank Accession No. AB009255.

1.6 DNA-binding domain (DPD) of poly(ADP-ribose) polymerase (PARP): The DBD (1.1 kb) may be obtained from plasmid pPARP6 by XbaI/SalI digest; Küpper et al., J. Biol. Chem. (1990), Volume 265, 18721-18724.

1.7 CVB3 protease 2A: The sequence coding for the cytotoxic pro-tease 2A is obtained from plasmid pIND-2A of the applicant by Pme digest.

1.8 CVB3 protease 3C: The sequence coding for the cytotoxic protease 3C is obtained from plasmid pIND-3C of the applicant by Pme digest.

Klump et al. describe the complete CVB3-cDNA sequence in J. Virol. (1990), Volume 64, 1573-1583; GenBank Accession No. M33854; protein 2A: Nucleotide 3304-3744; protein 3C: Nucleotide 5362-5910.

1.9 Fusion genes: A fusion gene means the continuous sequence of a therapeutic gene composed of several, preferably two, cDNAs which are expressed via a single promoter to give a continuous fusion protein. In this way it is possible to transfer simultaneously two therapeutic principles, thus resulting in additive or synergistic effects in the therapy.

In order for the protein domains of the fusion partners to be able to fold optimally for application, the information for a short peptide linker, preferably for glycine, in particular 8-10 glycines, is cloned between the cDNAs.

In this way, the following fusion genes are generated: CD-linker-HSV-TK, CD-linker-DBD, CD-linker-2A, CD-linker-3C, HSV-TK-linker-DBD, HSV-TK-linker-2A, HSV-TK-linker-3C, DBD-linker-2A and DBD-linker-3C. The order of the fusion partners within a fusion gene may also be reversed.

1.10 T7 RNA polymerase (T7 Pol): The T7 Pol cDNA (2.6 kb) originates from plasmid pAR3132 of the applicant and contains codons 11-883 of the T7 RNA-polymerase gene.

The sequences of the building blocks have been deposited with the PubMed gene bank of the National Library of Medicine (http://ww4.ncbi.nlm.nih.gov/Pub-Med/).

EXAMPLE 2

Preparation of Recombinant Adenoviruses

Recombinant adenoviruses are prepared by using, for example, the E1/E3-deleted adenovirus-5 system of Vogelstein; He et al., PNAS (1998), Volume 95, 2509-2514.

The cDNA to be expressed, i.e. the therapeutic gene, is cloned into vector pShuttle (6.7 kb). The promoter (telomerase or cyclin-A) intended for application is cloned in front of the cDNA and a polyadenylation signal is cloned behind the cDNA. The newly generated plasmid is transformed together with the pAdEasyl helper plasmid into the recombination-competent bacterial strain BJ5183.

Homologous recombination of the overlapping shuttle- and helper-vector sequences results in a recombinant adenoviral genome which is isolated from the bacteria and transformed into the recA-strain HB101 for preparative processing. Plasmid material is then isolated from the said bacteria on the preparative scale and purified via caesium chloride centrifugation.

The plasmid material obtained is transfected into the E1-expressing helper cell line 911; Fallaux et al., Hum. Gene Ther. (1996), Volume 7, 215-222. After transfection with the recombinant adenoviral genome, the cells are overlaid with soft agar. The virus then propagates in transfected cells and a plaque is formed from which the recombinant viruses can be isolated by freeze-thaw lysis. Expression can be detected after two days but no cytopathic effect (CPE) is apparent yet. Virus stocks are obtained by infecting new 911 cells with the appropriate recombinant adenoviruses. After approx. four days, the CPE has fully formed. The cells are disrupted in a Dounce homogenizer, cell debris is pelleted by short centrifugation and the viruses present in the supernatant are purified via caesium chloride density-gradient centrifugation.

The adenovirus vector obtained in this way is depicted in FIG. 1, top, and the abbreviations used are explained in the legend to the figures.

EXAMPLE 3

Preparation of Recombinant Adeno-Associated Viruses (AAV)

An example of the system used here is the system of Samulski, comprising two plasmids plus adenovirus; Snyder et al.: "Production of recombinant adeno-associated viral vectors". Current Protocols in Human Genetics. New York: John Wiley and Sons (1996), 12.1.1-12.1.24.

The cDNA to be expressed, i.e. the therapeutic gene, is cloned together with regulatory sequences (promoter and poly-A signal) into a vector containing only AAV-2 terminal repeats. These repeats are the minimum Cis-regulatory sequences required for replication and packaging; Xiao et al., J. Virol. (1997), Volume 71, 941-948.

The vector is generated by excising the rep/cap sequence via XbaI digest from plasmid pSub201 (Human Gene Therapy Center, University of North Carolina, Chapel Hill, N.C., USA). The terminal repeats of in each case 0.18 kb remain in the vector.

The building blocks intended for the particular gene transfer system, such as promoter, cDNA of the therapeutic gene and polyadenylation signal, are then cloned into said vector. The vector plasmids thus generated are transfected into 293-cells, in each case together with the pAAV/Ad (Human Gene Therapy Center) helper plasmid which provides the AAV structural and non-structural proteins (cap and rep) in trans. On the next day, wild-type adenovirus is added as a helper for AAV replication to the cells at an MOI of 3. Two to three days after transfection/infection, the cytopathic effect (CPE) is well visible and recombinant AAV can be obtained from the cells.

The caesium chloride purification method is carried out as described by Snyder et al., loc. cit. Essential elements of this AAV purification are three times freeze-thaw lysis of the infected cells plus ultrasound treatment to release the viruses, ammonium sulphate precipitation to remove cellular proteins, purification of the AAV particles on a CsCl gradient by ultracentrifugation, dialysis of the purified AAV fractions by PBS and heat-inactivation of contaminating adenoviruses by incubation at 56° C. for 15 minutes (AAV is not inactivated by this treatment).

The AAV vector obtained in this way is depicted in FIG. 1, centre.

EXAMPLE 4

Preparation of Recombinant Retroviruses

An example of a system which may be used here is the system from Clonetech (Heidelberg). This system comprises shuttle vectors, for example pLNCX (6.2 kb), which can be propagated via transformation into bacteria and also a helper cell line, the RetroPack PT67 line, which enables transcomplementation of the vectors to virions.

Prior to using the pLNCX shuttle vector, the CMV promoter is removed from this vector in order to be replaced thereafter by the promoter of choice, i.e. the telomerase promoter or the cyclin-A promoter. The abovementioned therapeutic genes or fusion genes are then cloned into the multiple cloning sequence with polyadenylation signals.

The recombinant vector is transfected into the packaging cell line PT67. Transfected cells can be selected for by using the antibiotic G418. As a result, recombinant retroviruses are produced, which are obtained from cells and cell culture supernatant via methods analogous to those described in Examples 2 and 3 and which can be purified by caesium chloride density-gradient centrifugation.

The retrovirus vector obtained in this way is depicted in principle in FIG. 1, bottom.

EXAMPLE 5

Adenovirus Vector with Positive-Feedback System

Figure 2:
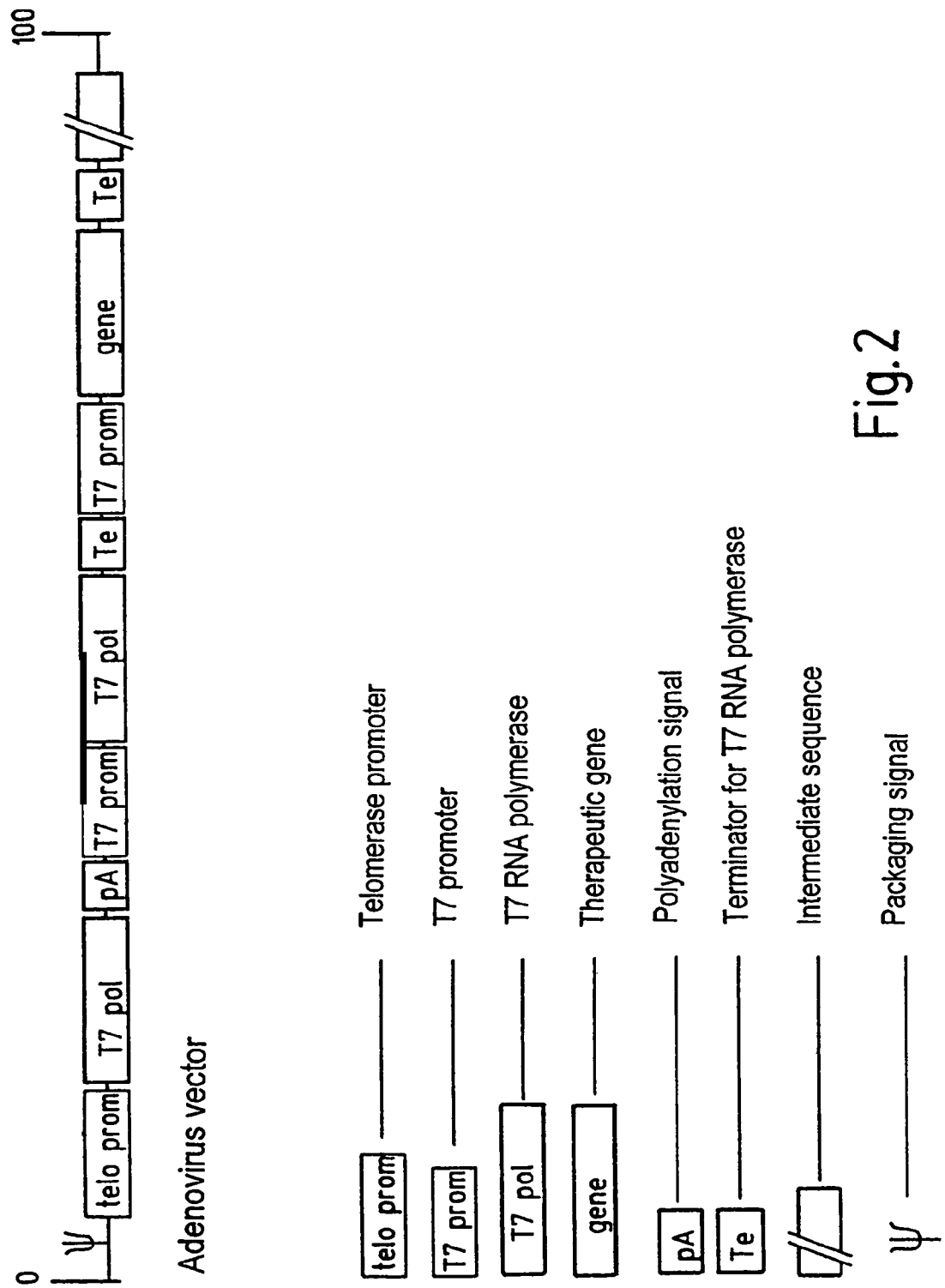
FIG. 2 shows viral vectors with positive-feedback expression of therapeutic genes in tumor cells.

FIG. 2 depicts an adenovirus vector which was prepared as de-scribed in Example 2. However, instead of a single promoter and a single therapeutic gene, this vector contains three expression units, the first of which contains T7 RNA polymerase under the control of the telomerase promoter. The second expression unit likewise contains T7 RNA polymerase but under the control of its own promoter, the T7 promoter. Finally, the third expression unit contains the therapeutic gene under the control of the T7 promoter.

When target cells are infected, first the telomerase promoter causes expression of T7 RNA polymerase (first expression unit). The T7 RNA polymerase generated "switches on" the T7 promoter in the second expression unit, so that this T7 promoter, too, causes T7 RNA-polymerase production. This results in a positive-feedback system, and the more T7 RNA polymerase is generated, the more T7 promoter is switched on.

In this way, expression of the therapeutic gene which here is under the control of a T7 promoter is increased.

In this system, the telomerase promoter thus controls expression of the therapeutic gene not directly, as in Examples 2-4, but in-directly via the intermediate step of the positive-feedback sys-tem of T7 promoter and T7 RNA polymerase.

Since the T7 promoter is silent in eukaryotic cells without the T7 RNA polymerase which usually is not found there, the therapeutic gene consequently can be expressed only in those cells in which the telomerase promoter is active, i.e. especially in tumor cells.

What is claimed is:

1. A vector for treating tumors by gene therapy, comprising a DNA sequence comprising
    a) a first sequence encoding T7 RNA polymerase under control of a tissue-specific promoter that is a telomerase catalytic subunit promoter or a cyclin-A promoter;
    b) at least one therapeutic gene under control of a first T7 promoter, wherein the therapeutic gene encodes a protein selected from the group consisting of: cytosine deaminase (CD), herpes simplex-virus thymidine kinase (HSV-TK), DNA-binding domain (DBD) of poly(ADP-ribose) polymerase (PARP), cytotoxic protease 2A and 3C; or a fusion protein comprising at least two proteins selected from the group of proteins; and
    c) a second sequence encoding T7 RNA polymerase under control of second T7 promoter.

2. The vector of claim 1, wherein the therapeutic gene codes for a protein selected from the group of proteins consisting of: cytosine deaminase (CD), herpes simplex-virus thymidine kinase (HSV-TK), DNA-binding domain (DBD) of poly(ADP-ribose) polymerase (PARP), cytotoxic protease 2A and 3C.

3. The vector of claim 2, wherein said cytotoxic protease 2A and 3C is from picornaviruses.

4. The vector of claim 2, wherein said cytotoxic protease 2A and 3C is from group B Coxsackie viruses.

5. The vector of claim 2, wherein said cytotoxic protease 2A and 3C is from group B Coxsackie viruses, serotype B3.

6. The vector of claim 1, wherein the therapeutic gene is a fusion gene coding for a fusion protein of at least two proteins selected from the group of proteins.

7. The vector of claim 6, wherein the therapeutic gene between the sequence regions for the two proteins codes for a peptide linker.

8. The vector of claim 7, wherein the linker comprises glycine.

9. The vector of claim 8, wherein the linker comprises between 8-10 glycines.

10. The vector of claim 7, wherein the fusion gene is selected from the group consisting of: CD-linker-HSV-TK, CD-linker-DBD, CD-linker-2A, CD-linker-3C, HSV-TK-linker-DBD, HSV-TK-linker-2A, HSV-TK-linker-3C, DBD-linker-2A and DBD-linker-3C.

11. The vector of claim 1, comprising a virus vector.

12. The vector of claim 1, comprising an adenovirus vector.

13. The vector of claim 1, comprising an adeno-associated virus (AAV) vector.

14. A retrovirus, coding for a vector of claim 1.

15. A method for treating tumors by gene therapy, comprising the step of administering to an individual in need of such therapy a vector of claim 1.

16. The method of claim 15 for treating neoplastic disorders.

17. The method of claim 15, further comprising the step of treating the individual with radio-therapy.

18. The method of claim 15, further comprising the step of treating the individual with a therapy with cytostatics.

19. A method for treating benign tumors, comprising the step of administering to an individual in need of such treatment the vector of claim 1, wherein the tissue-specific promoter is the cyclin-A promoter.

20. The method of claim 19 for treating recurring stenoses.

* * * * *

```
                       SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Forward primer for telomerase promoter

<400> SEQUENCE: 1
atcagctttt caaagacaca c                                              21

<210> SEQ ID NO 2
<211> LENGTH: 21
<212> TYPE: DNA
<213> ORGANISM: Artificial Sequence
<220> FEATURE:
<223> OTHER INFORMATION: Reverse primer for telomerase promoter

<400> SEQUENCE: 2 cgcggggtg gccggggcca g                                               21

<210> SEQ ID NO 3
<211> LENGTH: 21
<212> TYPE: DNA
<213> ORGANISM: Artificial Sequence
<220> FEATURE:
<223> OTHER INFORMATION: Forward primer for Cyclin-A promoter

<400> SEQUENCE: 3
cgtgttaaat aatttatgca c                                              21

<210> SEQ ID NO 4
<211> LENGTH: 21
<212> TYPE: DNA
<213> ORGANISM: Artificial Sequence
<220> FEATURE:
<223> OTHER INFORMATION: Reverse primer for Cyclin-A promoter

<400> SEQUENCE: 4
cactgctccc gggagtggac g                                              21
```